United States Patent [19]

Mazzafro et al.

[11] Patent Number: 5,902,910
[45] Date of Patent: May 11, 1999

[54] WEAK ACID PROCESS FOR PRODUCING DINITROTOLUENE

[75] Inventors: William Joseph Mazzafro, Schnecksville; Stephen Ian Clarke, Macungie; Mark Shedric Simpson, Germansville; Richard Van Court Carr, Allentown, all of Pa.

[73] Assignee: Air Products and Chemicals, Inc., Allentown, Pa.

[21] Appl. No.: 08/933,706

[22] Filed: Sep. 19, 1997

[51] Int. Cl.⁶ .................................................. C07C 205/00
[52] U.S. Cl. ............................................ 568/934; 568/932
[58] Field of Search ...................... 568/934, 932

[56] References Cited

U.S. PATENT DOCUMENTS

| | | | |
|---|---|---|---|
| 2,475,095 | 7/1949 | Hoek | 260/645 |
| 2,947,791 | 8/1960 | Adams | 260/645 |
| 3,087,971 | 4/1963 | Samuelsen | 260/645 |
| 3,157,706 | 11/1964 | Ozeki | 260/645 |
| 3,204,000 | 8/1965 | Sammuelsen | 260/645 |
| 4,022,844 | 5/1977 | De Cazenove et al. | 568/932 |
| 4,496,782 | 1/1985 | Carr | 568/934 |
| 5,345,012 | 9/1994 | Schieb et al. | 568/934 |

*Primary Examiner*—Paul J. Killos
*Assistant Examiner*—J. Parson
*Attorney, Agent, or Firm*—Russell L. Brewer

[57] ABSTRACT

This invention relates to an improved process for the production of dinitrotoluene wherein one is able to effectively employ a feed sulfuric acid, which is referred to as "weak acid" as the feed sulfuric acid for the nitration facility. The weak acid concentration, as feed, ranges from 86–91%, preferably 87–89% sulfuric acid by weight, to meet the total sulfuric acid requirements for the facility. This is accomplished by utilizing cocurrent processing in a mononitration zone and countercurrent nitration with respect to sulfuric acid in the dinitration zone.

13 Claims, 2 Drawing Sheets

WEAK ACID PROCESS FOR PRODUCING DINITROTOLUENE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Dinitrotoluene is an important intermediate in producing toluenediisocyanate based polyurethanes. One of the conventional processes for producing dinitrotoluene is referred to as the mixed acid nitration process wherein toluene is reacted with nitric acid in the presence of sulfuric acid in a mononitration zone to produce the intermediate product, mononitrotoluene (MNT), which then is separated from the spent acid and the recovered mononitrotoluene contacted with nitric acid in the presence of sulfuric acid to form dinitrotoluene in a dinitration zone. Dinitrotoluene (DNT) then is separated from the aqueous phase and the spent sulfuric acid purified and concentrated. Typical, product specifications (weight %) for commercial grade dinitrotoluene generally will be greater than 98.5% dinitrotoluene, less than 0.1% mononitrotoluene, less than 0.1% trinitrotoluene, less than 0.1% by-products, less than 1.0% water and yield of toluene to dinitrotoluene greater than 98% at conversion levels of >99.9%. The isomer content of product DNT contains a minimum of 95% (on a water free basis) 2,4-plus 2,6-isomer with the balance of the DNT being made up of 2,3-; 3,4-; 2,5-; and 3,5-isomers. The normalized 2,4-plus 2,6-isomer content is between 79.0–81.0% 2,4-isomer and between 19.0–21.0% 2,6-isomer.

Commercially, toluene is converted to mononitrotoluene employing a "cycle acid" having an approximate concentration of from 0.5 to 2% by weight nitric plus nitrous acid and from 80 to 84% by weight sulfuric acid (all acid concentrations are on an organic free basis). Cycle acid s the spent sulfuric and nitric acid recovered from the dinitration zone and used for the nitration of toluene in the mononitration zone. The reaction product from the mononitration zone is separated into an organic phase and a spent acid phase that is recovered for purification and concentration to feed acid strength. The spent acid from the mononitrators typically contains from 0.2–1.5% by weight nitric plus nitrous acid and from 70 to 74% by weight sulfuric acid. The organic phase from the mononitration zone which contains a mixture of toluene, MNT, and DNT is fed to the dinitration zone and is contacted with additional mixed acid where the reaction to form DNT is essentially completed. Mononitrotoluene is typically converted to dinitrotoluene at mixed acid reaction concentrations of from 0.5 to 2% by weight nitric plus nitrous acid and from 80 to 84% by weight sulfuric acid.

Two moles of water are produced for each mole of dinitrotoluene produced, Accordingly, the concentation of feed nitric acid and feed sulfuric acid for the plant must be substantially greater than the concentration of nitric and sulfuric acid in the cycle acid. To meet the sulfuric acid requirements of commercial plants and produce commercial grade dinitrotoluene for the mixed acid nitration process, the feed sulfuric acid concentration has been within a range of approximately 93–98% or higher, generally above 95% by weight when used with subazeotropic nitric acid. Subazeotropic nitric acid has a concentration range from about 57 wt. % up to 69 wt. % nitric acid with nitric acid concentrations of 60–65 wt. % being typical for nitric acid used for the production of dinitrotoluene. Concentrations of >69% nitric acid require more costly methods of concentration, such costs are primarily associated with overcoming the azeotrope.

In a commercial DNT plant, the concentration of sulfuric acid in the cycle acid is set by the concentration of the feed sulfuric acid and feed nitric acid and the concentration of sulfuric acid in the spent acid from the mononitration zone. For a given concentration of sulfuric acid in the spent acid obtained from the mononitration zone, the concentration of sulfuric acid in the cycle acid will decrease as the concentration of feed sulfuric acid and the concentration of feed nitric acid decrease. Typically, the concentration of sulfuric acid in the cycle acid will have to be greater than 80 wt. % to yield a spent acid from the mononitration zone having a concentration of sulfuric acid ranging from about 70 to 74% by weight. There are essentially two problems associated with the generation of a spent acid from the mononitration zone having a sulfuric acid greater than about 74%, they are: it requires increased sulfuric acid usage, and it creates problems associated with the purification and concentration of the spent acid to feed sulfuric acid strength. Sulfuric acid concentrations lower than about 70% by weight result in excessive by-product formation and low conversions of toluene to mononitrotoluene.

Spent sulfuric acid recovered from the mononitration zone which has been diluted by virtue of the production of two moles of by-product water in the process has to be purified and concentrated to be reused for nitration. Typically, nitric acid, nitrous acid and organics in the spent acid are removed prior to concentration. One of the conventional ways to effect concentration of the spent sulfuric acid has been via a series of multiple-effect evaporators operating under vacuum. The concentration of spent sulfuric acid imposes substantial energy requirements upon the nitration facility, not to mention the environmental control problems associated with avoidance of volatile sulfur oxide emission from multi-stage evaporators. Control of environmental loss of sulfuric acid becomes more difficult as the concentration of the product sulfuric acid increases. These losses can become increasingly significant at a concentration above 89% sulfuric acid. Capital and operating costs associated with the evaporators and vacuum equipment are high ever for increases of 1% acid strength and greater when producing sulfuric acid of strengths greater than 89%.

Representative patents which show the production of nitroaromatics including dinitrotoluene and the concentration of spent sulfuric acid to feed acid strength are as follows:

U.S. Pat. No. 3,204,000 discloses the continuous, countercurrent nitration of toluene through a plurality of stages to produce trinitrotoluene. In a multi-stage, countercurrent process a mixture of concentrated nitric acid and oleum is fed to the final nitrator to effect final nitration of the toluene. The spent acid which has been diluted by the production of water is cycled to stages upstream of the final nitrator and thus the feed toluene which enters the first nitrator is contacted with the most dilute or weakest acid mixture. To avoid undesired oxidation of trinitrotoluene and dinitrotoluene by nitrous acid in the process, the aqueous phase and the organic phase are separated after intermediate stages of nitration in order to remove nitrous acid.

U.S. Pat. No. 3,087,971 discloses a continuous process for producing nitroaromatics coupled with a simultaneous reduction in by-product due to oxidation losses. The process is conducted such that the sulfuric acid concentration is maintained within a level of from 86–95%, the nitric acid is maintained within a range of about 14% and the water is maintained within a range of from 0–13.5% on a weight basis. Dinitration is effected in at least two steps in which from 60 to 75% of the sulfuric acid requirements and up to 20% but not more than 30% of the nitric acid requirements for trinitrotoluene are available for the last step. In the last step where trinitrotoluene is produced, the balance of the nitric acid and sulfuric acid is introduced as a mixture of concentrated nitric and oleum with at least 20% free $SO_3$. Thus, the trinitrotoluene product is withdrawn in an acid mixture nearly free of water. The feed acid to the facility to maintain reactor concentration is oleum containing 25% free $SO_3$.

U.S. Pat. No. 2,475,095 discloses a continuous process for the production of trinitrotoluene with the nitration process divided into three divisions. In the first division mononitrotoluene is formed, in the second division the mononitrotoluene is converted to a mononitro/dinitrotoluene mixture, and in the third stage the mixture of mono and dinitrotoluene is converted into trinitrotoluene. A composition at the end of the first stage is shown to comprise 71% $H_2SO_4$, 25% $H_2O_1$, 1% $HNO_3$, in the second stage the concentration is shown to comprise 78% $H_2SO_4$, 15% $H_2O_1$, 2% $HNO_3$, and 3% nitro-products. At the end of the third stage the concentration is shown to comprise 81% $H_2SO_4$, 3% $H_2O_1$, 6% $HNO_3$ and 7% dissolved trinitrotoluene. Mixed acids having at least 30% free $SO_3$ and at least 30% nitric acid are preferred as the feed acid starting material.

U.S. Pat. No. 3,157,706 discloses a process for producing dinitrotoluene wherein it was found that if the concentration of sulfuric acid was higher than 65%, trinitrotoluene was produced. The process comprises nitrating mononitrotoluene with a mixed acid consisting of 33–36% by weight nitric acid, 60–65% by weight sulfuric acid and the remainder water.

U.S. Pat. No. 2,947,791 discloses a process for producing both mono and dinitrotoluene by the mixed acid nitration method. In that process toluene is continuously nitrated to form mononitrotoluene in a two reactor system which then is subsequently nitrated to a dinitrotoluene product in the form of a mixture containing approximately an 80:20 ratio of 2:4-/2:6-dinitrotoluene isomers. The nitrating mixture contains about 50–60% sulfuric acid, 20–40% nitric acid and 10–20% water. The mixture is prepared by blending 95% nitric acid with a spent sulfuric acid solution. The spent sulfuric acid from the second reactor contains from about 62–75% sulfuric acid.

U.S. Pat. No. 4,496,782 discloses a process for recovering nitric acid from the mononitration of toluene wherein toluene is reacted with nitric acid in the presence of sulfuric acid to form mononitrotoluene. To recover the value of the nitric acid in the spent acid, the mononitrotoluene is subsequently adiabatically nitrated in the presence of the spent acid in a dinitration reactor.

U.S. Pat. No. 5,345,012 discloses a process for producing dinitrotoluene by a single stage nitration of toluene under adiabatic conditions. The examples show the nitration of toluene utilizing a mixture of sulfuric acid and nitric acid where the molar ratio of nitric acid to toluene is slightly greater than 2:1. The nitrating acid is comprised of inorganic components consisting of 60–90% by weight sulfuric acid and 1–15% nitric acid.

BRIEF SUMMARY OF THE INVENTION

This invention relates to an improved process for the production of dinitrotoluene. By the practice of the process described herein one is able to effectively employ a feed sulfuric acid, which is referred to as "weak acid" as the feed sulfuric acid for the nitration facility. The weak acid process employs a feed sulfuric acid having a concentration which ranges from 86–91%, preferably 87–89% sulfuric acid by weight, to meet the total sulfuric acid requirements for the facility.

In terms of effecting dinitration of toluene, the "weak acid process" has the following advantages:

an ability to reduce the steam requirements from ~2.7$^+$ lb steam per lb. water removed for the conventional process to ~1.9. lb. steam per pound of water removed in concentrating the sulfuric acid to the feed concentration level:

an ability to produce dinitrotoluene meeting commercial product specification and conversion levels;

an ability to produce dinitrotoluene with excellent reaction rates and without producing excess trinitrotoluene or oxidation products;

an ability to utilize a subazeotropic nitric acid having a concentration of 57–69 weight % and thus avoid the necessity of moving to higher and more costly nitric acid concentrations, e.g., 90–98 weight %, although in the alternative such high concentrations may be used with weak sulfuric acid, as desired, to enhance capacity for the plant;

an ability to reduce the capital cost of the sulfuric acid concentration unit by operating at a higher pressure thereby reducing the size of this unit and the evaporator heat transfer area can be lower due to the lower viscosity of the boiling acid;

an ability to effect dinitration without generating substantial quantities of by-products which often are in the form of non-recoverable oxidation products or nitration by-products; and, an ability to effect dinitration with a lower concentration of nitric acid in the final nitration stage thereby reducing the amount of nitric acid loss due to the solubility of nitric acid in the DNT.

DETAILED DESCRIPTION OF THE INVENTION

Figure 1:
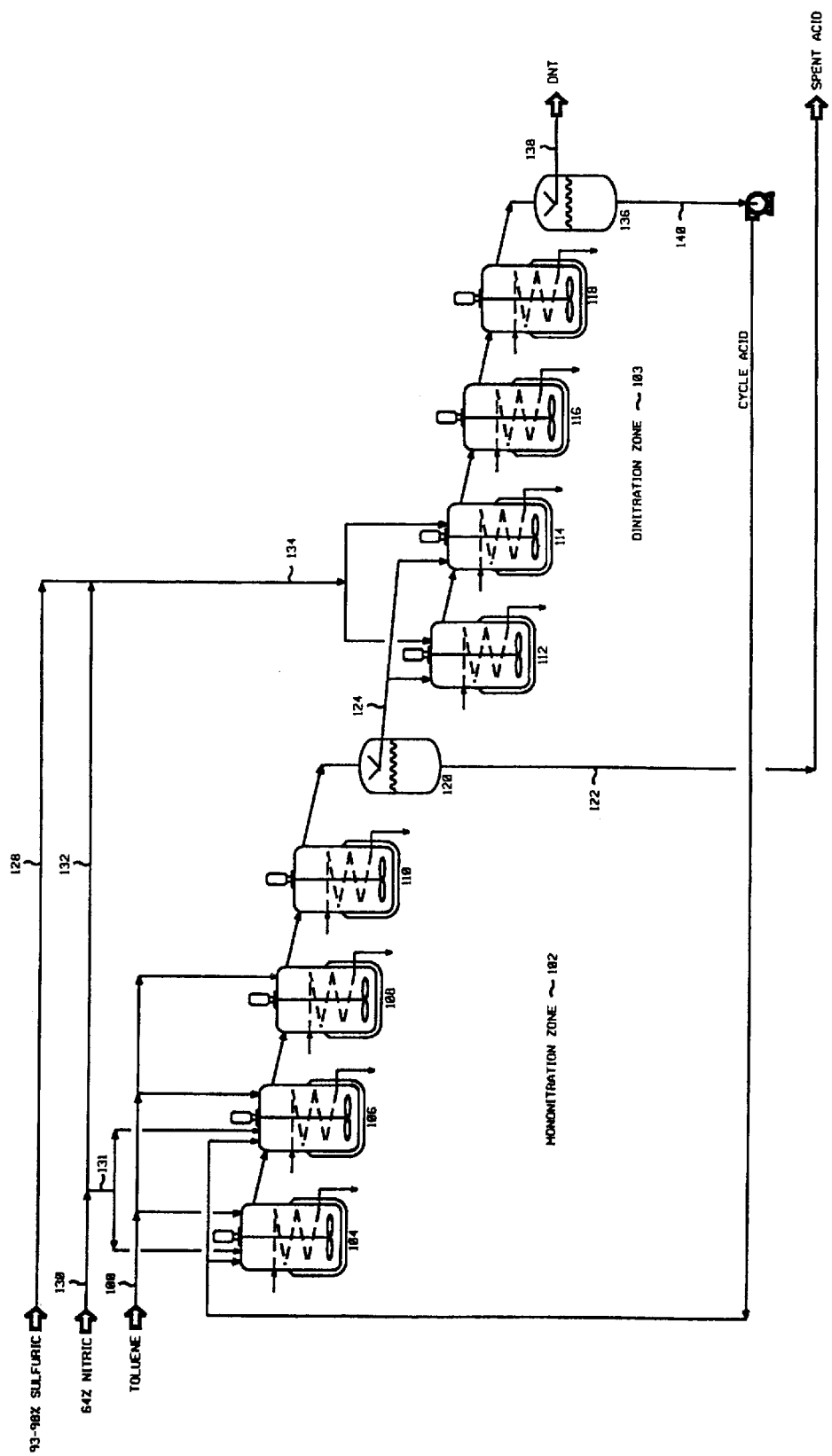
FIG. 1 is a flow diagram of a prior art, cocurrent process for producing mononitrotoluene, followed by a cocurrent process for producing dinitrotoluene.
Figure 2:
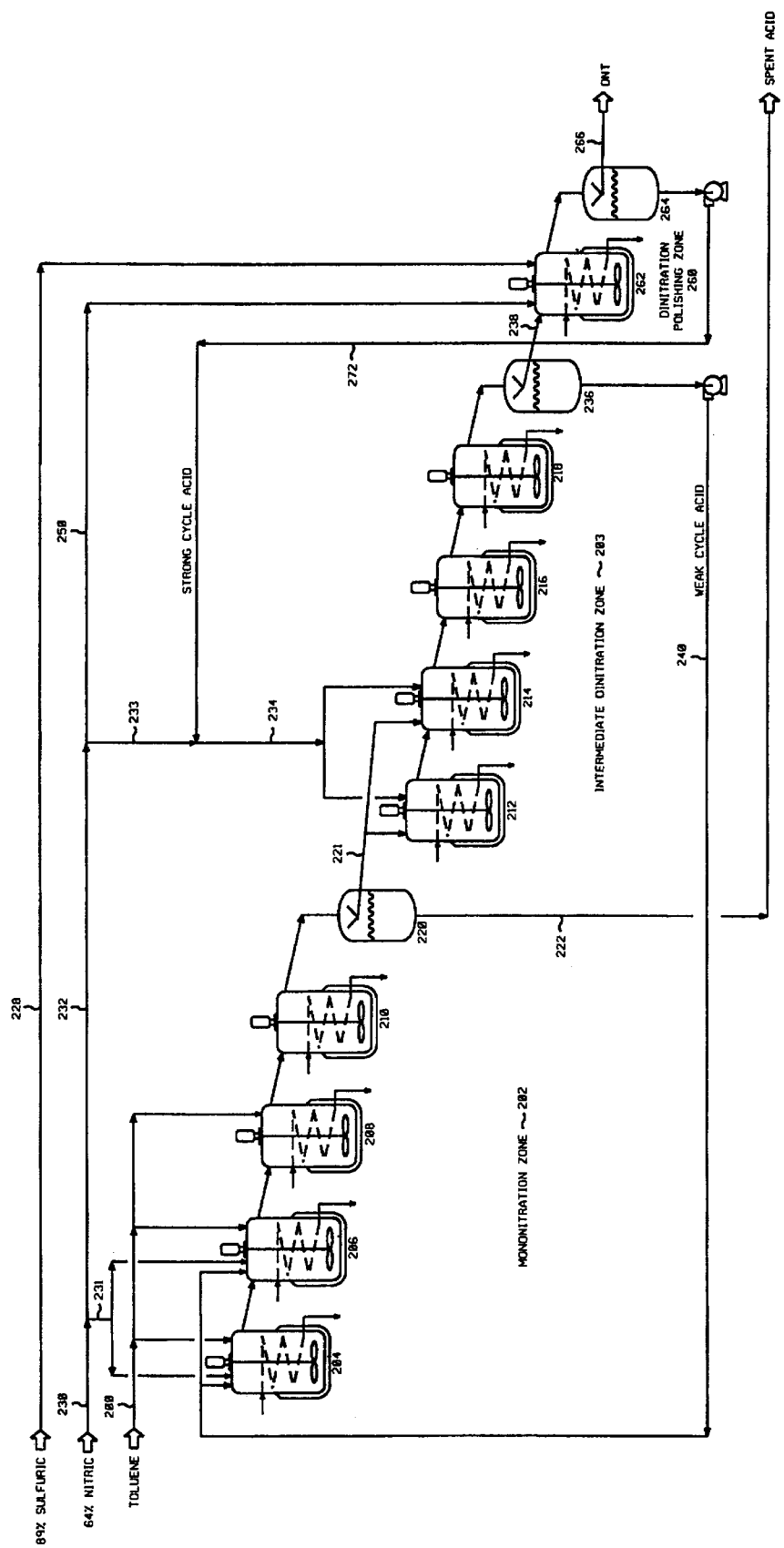
FIG. 2 is a flow diagram of an embodiment of the weak acid process which comprises a combination cocurrent/countercurrent process, a cocurrent process for producing mononitrotoluene and a countercurrent process contemplated for dinitrotoluene synthesis which incorporates a dinitrotoluene polishing zone.

To facilitate an understanding of the prior art and the improved weak acid process for the dinitration of toluene, reference is made to FIGS. 1 and 2 with FIG. 1 representing a typical, commercial prior art process while FIG. 2 represents the "weak acid" process (as used herein all acid concentrations are on an organic free basis). For purposes of convenience. FIG. 1 employs a 100 series of numbers while FIG. 2 employs a 200 series of numbers with similar equipment components in each process having identical numbers but for the series designation. For example, apparatus 120 is the same as apparatus 220 but for the figure designation.

FIG. 1 discloses a cocurrent, prior art process for producing commercial grade dinitrotoluene having a mononitration zone 102 and a dinitration zone 103. The mononitration is carried out in a series of four stirred tank nitration reactors 104, 106, 108 and 110 that are typically of equal size. The toluene feed via line 100 is split between the first three mononitration to distribute the heat load. The cycle acid via line 140 and feed nitric acid of 57–69% by weight preferably 60–65% by weight via streams 130 and 131 are also split between the first two mononitrators usually with a higher percentage of acids going to the first mononitrator than toluene. (The number of reactors and feed splits are not critical to the process; it is a matter of design.) The conversion of toluene to mononitrotoluene is from about 95 to 100 mole percent in the mononitration zone 102. Approximately, 85 to 95 mole percent toluene is converted in mononitration reactors 104 and 106 with the effluent from these mononitration reactors charged, as shown, first to mononitration reactors 108 where the molar conversion ranges from 60 to 80 percent of the unreacted toluene and then the effluent sent to mononitration reactor 110 for completing the conversion of toluene to mononitrotoluene. The sulfuric and nitric plus nitrous acid concentrations on a weight basis in mononitration reactors 102 and 104 typically will range from 70 to 76 weight percent sulfuric acid and 0.5 to 4.0 weight % nitric plus nitrous acid. The concentration of sulfuric and nitric plus nitrous acid on a weight basis in mononitration reactors 108 and 110 typically will range from 70 to 74 weight % sulfuric acid and 0.2 to 1.5 weight % nitric plus nitrous acid. The residence time in mononitration zone 102 ranges from 5 to 30 minutes. Mononitration is usually carried at temperatures between 110° F. and 150° F.

Mononitration is essentially complete in mononitration reactor 110. The overflow from mononitration reactor 110 is sent to a phase separator 120 wherein a first spent acid is withdrawn from the bottom of the phase separator 120 through line 122 and the organic phase comprising mostly mononitrotoluene is withdrawn as an upper layer for further processing. The spent acid is withdrawn via line 122 for purification and concentration to feed acid strength.

Dinitration zone 103 has a series of four stirred tank nitration reactors 112, 114, 116, and 118 that are typically of equal size. The organic phase from the mononitrotoluene zone is removed from phase separator 120 via line 124 and sent to the dinitration zone 103. The organic phase via line 124 and the acid feed via line 134 can be split between the first two dinitration reactors to spread the heat load. The percentage of total acid split to the first dinitrator is typical greater than the percentage of the organic feed split to the first dinitrator. (The number of reactors and feed splits are not critical to the process; it is a matter of design.).

Feed sulfuric acid having a concentration ranging from 93–98%, preferably greater than 95% by weight, is introduced through line 128 to dinitration reactors 112 and 114. Feed nitric acid having a concentration of about 57–69% by weight, preferably 60–65% by weight, is introduced through line 130 and 132 and combined with the sulfuric acid in line 134, cooled and then introduced to dinitration reactors 112 and 114. Alternatively, the nitric and sulfuric acid can be charged directly to the reactors. Cocurrent flow is from dinitration reactors 112 and 114 to dinitration reactor 116 and then to dinitration reactor 118.

The concentration of sulfuric and nitric plus nitrous acid on a weight basis in dinitration reactors 112 and 114 typically will range from 81 to 86% sulfuric acid and 1.5 to 6.0% nitric plus nitrous acid on a weight basis. The concentration of sulfuric and nitric plus nitrous acid on a weight basis in dinitration reactors 116 and 118 will range from 80 to 85% sulfuric acid and from 0.5 to 2.0% nitric plus nitrous acid. Molar conversion of mononitrotoluene is from 85 to 98% in dinitration reactors 112 and 114, from 70 to 93% in dinitration reactor 116 and then in dinitration reactor 118 to a final conversion of from 60 to 80%. A residence time of from 5 to 30 minutes is customary for converting mononitrotoluene to dinitrotoluene. Dinitration is carried out to achieve a mononitrotoluene conversion of 99.9 to 100 mole % based on mononitrotoluene. Dinitration is usually carried out at temperatures between 160° F. and 180° F.

The dinitrotoluene product is withdrawn from dinitration reactor 118 and charged to phase separator 136 wherein a second spent acid is separated from the organic phase. The crude dinitrotoluene in the reaction product then is conveyed via line 138 to a purification section (not shown) for purification. The second spent acid forms cycle acid which is withdrawn via line 140 and charged to the mononitration zone 102.

Referring to FIG. 2 it is noted that the process differs in that it incorporates what is referred to as a dinitrotoluene polishing zone designated 260 which comprises at least one dinitration polishing reactor 262. In that sense, one can view the FIG. 2 process as having a one cocurrent zone, i.e., a mononitrotoluene zone 202 as in FIG. 1, but having a countercurrent flow with respect to sulfuric acid comprising an intermediate dinitration zone 203 and a dinitrotoluene polishing zone 260, the combination achieving dinitration of mononitrotoluene. In contrast to the prior art FIG. 1 process, by employing a countercurrent process in effecting dinitration, a feed acid of 86–91%, preferably 87–89% sulfuric acid by weight, can be utilized, as opposed to 93–98%, generally >95% sulfuric acid by weight can be utilized.

The mononitration is carried out in a series of four stirred tank nitration reactors 204, 206, 208 and 210 that are typically of equal size. The toluene feed via line 200 can be split between the first three mononitrators to distribute the heat load. The weak cycle acid via line 240 and feed nitric acid of 57–69% by weight preferably 60–65% by weight via lines 230 and 231 are also split between the first two mononitrators usually with a higher percentage of acids going to the first mononitrator than toluene. (The number of reactors and feed splits are not critical to the process; it is a matter of design.) The conversion of toluene to mononitrotoluene is >90% and preferably >95% mole percent in the mononitration zone 202. Approximately, 85 to 95 mole percent toluene is converted in mononitration reactors 204 and 206 and the effluent from these mononitration reactors charged, as shown, first to mononitration reactors 208 where the molar conversion ranges from 60 to 80 percent of the unreacted toluene and then the effluent sent to mononitration reactor 210 for completing the conversion of toluene to mononitrotoluene. The sulfuric and nitric plus nitrous acid concentrations on a weight basis in mononitration reactors 204 and 206 typically will range from 70 to 76 weight percent sulfuric acid and 0.5 to 4.0 weight % nitric plus nitrous acid. The concentration of sulfuric and nitric plus nitrous acid on a weight basis in mononitration reactors 208 and 210 typically will range from 70 to 74 weight % sulfuric acid and 0.2 to 1.5 weight % nitric plus nitrous acid. The residence time in mononitration zone 202 ranges from 5 to 30 minutes. Mononitration is usually carried at temperatures between 110° F. and 150° F.

Mononitration is essentially complete in mononitration reactor 210. The overflow from mononitration reactor 210 is sent to a phase separator 220 wherein a first spent acid is withdrawn from the bottom of the phase separator 220 through line 222 and the organic phase comprising mostly mononitrotoluene is withdrawn as an upper layer for further processing. The first spent acid is withdrawn via line 222 for purification and concentration to feed acid strength.

Feed subazeotropic nitric acid via line 233, of 57–69% by weight, preferably 60–65% by weight, in addition to at least a portion of "strong cycle acid" obtained as a third spent acid from the diritration polishing zone 260 via line 272, is mixed and then charged through line 234 to dinitration reactors 212 and 214. Alternatively, the nitric acid and strong cycle acid can be charged directly to the first two dinitrators. The organic phase via line 221 and the acid feed via line 234 can be split between the first two dinitration reactors to spread the heat load. The percentage of total acid split to the first dinitrator is typically greater than the percentage of the organic feed split to the first dinitrator. (The number of reactors and feed split are not critical to the process; it is a matter of design.) The effluent from reactor 214 is charged to dinitration reactor 216 and then the effluent from reactor 216 is charged to reactor 218. This series of reactors constitutes the intermediate dinitration zone. In contrast to the prior art, the molar conversion of mononitrotoluene to dinitrotoluene in the intermediate dinitration zone 203 is limited to a range from about 60 to 95% and preferably for about 80 to 90% based on mononitrotoluene. Thus, the organic layer from dinitration reactor 218 will comprise anywhere from about 70 to 97% by weight dinitrotoluene, 3 to 30% by weight mononitrotoluene and 0.2 to 0.5% by weight by-products in the form of nitrocresols and the like. The temperature for effecting dinitration ranges from 160–180° F.

At the conclusion of intermediate dinitration of the mononitration, the reaction product is conveyed to phase separator 236 and separated into an organic phase and a second spent acid referred to herein as "weak cycle acid" recovered. At least a portion is conveyed via line 240 and charged to mononitration zone 202. Surprisingly, the lower concentration of sulfuric acid in the weak cycle acid, i.e., the acid recycled for use in preparing mononitrotoluene from toluene in the mononitration zone did not substantially detract from the conversion of toluene to mononitrotoluene nor did it detract from the conversion of mononitrotoluene to dinitrotoluene to a high level, e.g., 80 to 95%. Heretofore, it was thought that dinitrotoluene formation would be severely impacted.

A key to the invention is that essentially complete conversion of dinitrotoluene without forming substantial levels of trinitrotoluene and other by-products can be effected in dinitration polishing zone 260. Feed nitric acid 57–69% by weight, preferably 60–65% by weight (stream 250), sulfuric acid of 86–91% by weight, preferably 87–89% by weight (stream 228), and the organic phase from the intermediate dinitration zone via stream 238 are charged to the polishing reactor 262 to effect a mixed acid reaction concentration ranging from 0.1 to 1.5% by weight nitric plus nitrous acid and 82 to 90% by weight sulfuric acid. Dinitration in the dinitrotoluene polishing zone 260 is effected at temperatures of from 160–180° F. The nitric acid and sulfuric acid may be mixed prior to charging to polishing reactor 262 or they may be charged as separate streams. The dinitrotoluene product is removed from dinitration polishing reactors 262 and sent to phase separator 264 wherein the organic layer and aqueous layer are separated thereby generating a third spent acid referred to as strong cycle acid. Dinitrotoluene is removed via line 266 for further purification (not shown) while the strong cycle acid is conveyed by line 232 to intermediate dinitration zone 203.

The following examples are provided to illustrate various embodiments on the invention and are not intended to restrict the scope thereof.

General Procedure:

Two nitrations were done to show the comparison between the prior art, cocurrent process and weak acid process. The same size nitrator is used in all examples.

COMPARATIVE EXAMPLE 1

The nitration was conducted in a process as shown in FIG. 1. The nitrators were all of an equal size. A toluene feed was split essentially equally to mononitration reactor 104 and mononitration reactor 106. The nitric acid feed to the mononitration zone was split 60% to reactor 104 and 40% to reactor 106. The cycle acid from the dinitration zone was split 75% to reactor 104 and 25% to reactor 106. (The extent of the splits was not critical and was done for ease of handling). All of the organic phase from phase separator 120 was fed to dinitration reactor 112. The acid feed strengths were:

Nitric Acid=62.5% wt.
Sulfuric Acid=98.0% wt.

Mononitration was conducted at a temperature of 110–120° F. and dinitration was conducted at 166–170° F.

The following Tables 1 and 2 provide a molar and weight basis material balance to show the effect of sulfuric and nitric acid concentration on conversion and product specifications.

TABLE 1 molar basis
(lb. moles/hour)

| Stream Number | Toluene 100 | Total Nitric 130 | Nitric Mono 131 | Nitric Di 132 | Sulfuric 128 | DNT to Wash 138 | Spent Acid 122 | MNT to Di Sec 124 | WCA To Mono 140 |
|---|---|---|---|---|---|---|---|---|---|
| Toluene | 97.7 | | | | | | | 0.46 | |
| MNT | | | | | | | 1.13 | 91.1 | |
| DNT | | | | | | 95.4 | 1.18 | 13.7 | 9.91 |
| HNO3 + HNO2 | | 205 | 100 | 104 | | 2.57 | 8.02 | 1.47 | 7.33 |
| H2SO4 | | | | | 308 | 4.36 | 304 | 0.20 | 304 |
| H2O | | | 430 | 211 | 219 | 34.2 | 1.50 | 657 | 3.38 | 339 |

TABLE 1-continued molar basis
(lb. moles/hour)

| Stream Number | Toluene 100 | Total Nitric 130 | Nitric Mono 131 | Nitric Di 132 | Sulfuric 128 | DNT to Wash 138 | Spent Acid 122 | MNT to Di Sec 124 | WCA To Mono 140 |
|---|---|---|---|---|---|---|---|---|---|
| Totals | 97.7 | 635 | 311 | 323 | 342 | 104 | 971 | 110 | 660 |

TABLE 2 weight basis
lb./hour

| Stream Number | Toluene 100 | Total Nitric 130 | Nitric Mono 131 | Nitric Di 132 | Sulfuric 128 | DNT to Wash 138 | Spent Acid 122 | MNT to Di Sec 124 | WCA To Mono 140 |
|---|---|---|---|---|---|---|---|---|---|
| Toluene | 8,999 | | | | | | | 42.6 | |
| MNT | | | | | | | 155 | 12,489 | |
| DNT | | | | | | 17,370 | 214 | 2,503 | 1,805 |
| HNO3 + HNO2 | | 12,905 | 6,578 | 6,328 | | 162 | 505 | 92.8 | 462 |
| H2SO4 | | | | | 30,196 | 428 | 29,768 | 19.8 | 29,788 |
| H2O | | 7,743 | 3,947 | 3,797 | 616 | 27.0 | 11,831 | 60.8 | 6,104 |
| Totals | 8,999 | 20,649 | 10,524 | 10,124 | 30,812 | 17,986 | 42,474 | 15,208 | 38,158 |

WCA to mono refers to weak cycle acid recycled to the mononitration zone.

Toluene conversion in the mononitration zone was 99.5% with a residence time of 14.3 minutes. Mononitrotoluene conversion to dinitrotoluene was essentially 100% with a residence time of 14.4 minutes. The conversion of mononitrotoluene to dinitrotoluene in the first dinitrator was 97% and 90% in the second nitrator and third dinitrators. Since the reaction was essentially complete in the third dinitrator, conversion in the fourth dinitrator was not measurable. The spent acid from the mononitration zone and cycle acid composition on an organic free basis are set forth in Table 3.

TABLE 3

| | Spent Acid Stream 122 wt. % | Cycle Acid Stream 140 wt. % |
|---|---|---|
| Nitric plus Nitrous Acid | 1.2 | 1.3 |
| Sulfuric Acid | 70.7 | 81.9 |
| Water | 28.1 | 16.8 |

EXAMPLE 2
Nitration of Toluene to Produce Dinitrotoluene Using ~88% Sulfuric Acid The nitration was conducted in a process as shown in FIG. 2. As in Example 1, the nitrators were all of equal size. Toluene feed was split equally to reactors 204, 206 and 208. The nitric acid feed to the mononitration zone and cycle acid from the dinitration zone was fed to reactor 204. Two thirds of the organic phase from separator 220 was fed to reactor 212 and one third was fed to reactor 214. The acid feed strengths were:

Nitric Acid=62.4 wt. %.
Sulfuric Acid=87.3 wt. %

Mononitrotoluene was formed at a temperature of 116–135° F. and dinitrotoluene was formed in the intermediate dinitration zone at a temperature from 165 to 170° F. and about 165° F. in the dinitoluene polishing zone.

The following Tables 4 and 5 provide a molar and weight basis material balance to show the effect of suilfuric and nitric acid concentration on conversion and product specifications.

TABLE 4 molar basis
lb. moles/hr

| Stream No. | Toluene 200 | Total Nitric 230 | Nitric Mono 231 | Nitric Di 233 | Nitric Pol. 250 | Sulfuric 228 | DNT To Wash 266 | Spent Acid 222 | MNT to IDNT Sec 221 | IDNT To Pol. 238 | WCA To Mono 240 | SCA IDNT Sec. 272 |
|---|---|---|---|---|---|---|---|---|---|---|---|---|
| Toluene | 115 | | | | | | | | 3.92 | | | |
| MNT | | | | | | | | 1.31 | 102 | 13.2 | | |
| DNT | | | | | | | 113 | 0.90 | 14.9 | 135 | 8.59 | 35.7 |
| HNO3 + HNO2 | | 237 | 116 | 104 | 17.4 | | 0.48 | 8.13 | 0.94 | 0.48 | 11.3 | 4.28 |

TABLE 4-continued molar basis
lb. moles/hr

| Stream No. | Toluene 200 | Total Nitric 230 | Nitric Mono 231 | Nitric Di 233 | Nitric Pol. 250 | Sulfuric 228 | DNT To Wash 266 | Spent Acid 222 | MNT to IDNT Sec 221 | IDNT To Pol. 238 | WCA To Mono 240 | SCA IDNT Sec. 272 |
|---|---|---|---|---|---|---|---|---|---|---|---|---|
| H2SO4 |  |  |  |  |  | 605 | 1.83 | 603 | 0.50 | 1.83 | 604 | 605 |
| H2O |  | 498 | 244 | 218 | 36.7 | 478 | 1.73 | 1,203 | 3.84 | 1.73 | 845 | 528 |
| Totals | 115 | 735 | 359 | 322 | 54.1 | 1,083 | 117 | 1,816 | 126 | 152 | 1,469 | 1,173 |

TABLE 5 weight basis
lbs./hour

| Stream No. | Toluene 200 | Total Nitric 230 | Nitric Mono 231 | Nitric Di 233 | Nitric Pol. 250 | Sulfuric 228 | DNT To Wash 266 | Spent Acid 222 | MNT to IDNT Sec 221 | IDNT To Pol. 238 | WCA To Mono 240 | SCA IDNT Sec. 272 |
|---|---|---|---|---|---|---|---|---|---|---|---|---|
| Toluene | 10,573 |  |  |  |  |  |  |  | 361 |  |  |  |
| MNT |  |  |  |  |  |  |  | 178 | 14,032 | 1,804 |  |  |
| DNT |  |  |  |  |  |  | 20,499 | 163 | 2,714 | 24,607 | 1,565 | 6,504 |
| HNO3 + HNO2 |  | 14,923 | 7,296 | 6,528 | 1,099 |  |  | 30.3 | 512 | 58.9 | 30.3 | 714 | 270 |
| H2SO4 |  |  |  |  |  | 59,325 | 180 | 59,145 | 49.1 | 180 | 59,194 | 59,325 |
| H2O |  | 8,980 | 4,391 | 3,929 | 661 | 8,615 | 31.1 | 21,675 | 69.1 | 31.1 | 15,227 | 9,513 |
| Totals | 10,573 | 23,903 | 11,686 | 10,457 | 1,760 | 67,939 | 20,740 | 81,675 | 17,284 | 26,652 | 76,699 | 75,611 |

IDNT refers to the intermediate dinitrotoluene zone.

WCA refers to weak cycle acid charged to the mononitration zone.

SCA refers to strong cycle acid charged to the intermediate dinitration zone.

Toluene conversion (all conversions are molar) in the mononitration zone was greater than 96% with a residence time of 8.4 minutes. Mononitrotoluene conversion to dinitrotoluene in the dinitration zone was 88% with a residence time of 6.1 minutes. The conversion of mononitrotoluene to dinitrotoluene in the first dinitrator was 84%, 59% in the second nitrator and 29% in the third dinitrator. Since the conversion had dropped to such a low level in the third nitrator, the fourth dinitrator 218 was not used. (This conversion drop shows that the procedure of Example 1 would be unsatisfactory employing a feed of ~88% by weight sulfuric acid at the given flow rate; it could not be used to produce commercial grade dinitrotoluene. Substantially higher and impractical sulfuric acid flow rates would have to be employed in an effort to obtain desired sulfuric acid concentration strength in the cycle acid.) Polishing reactor 262 was used to complete the reaction. The conversion in polishing reactor 262 was 100% with no mononitrotoluene remaining in polishing reactor 262. The residence time in the polishing reactor was ~2.1 minutes. The total residence time to effect dinitration in dinitrators 212–216 and the polishing reactor 262 was 8.2 minutes.

The concentrations of sulfuric acid, and nitric acid in the first spent acid, weak cycle acid, and strong cycle acid composition on an organic free basis are shown in Table 6, they were:

TABLE 6

|  | Spent Acid Stream 222 wt. % | Weak Cycle Acid Stream 240 wt. % | Strong Cycle Acid Stream 272 wt. % |
|---|---|---|---|
| Nitric plus Nitrous Acid | 0.6 | 0.9 | 0.4 |
| Sulfuric Acid | 72.7 | 78.8 | 85.8 |
| Water | 26.7 | 20.3 | 13.8 |

What is claimed is:

1. In a process for producing dinitrotoluene by the mixed acid nitration of toluene wherein toluene is contacted with a mixture of nitric acid and sulfuric acid under nitration conditions to form mononitrotoluene in a mononitration zone, the reaction product separated into an organic phase containing mononitrotoluene and a first spent acid phase, and said organic phase containing mononitrotoluene introduced to a dinitration zone wherein it is contacted with a second mixture of nitric acid and sulfuric acid under nitration conditions to convert said mononitrotoluene therein to dinitrotoluene, the reaction product removed from the dinitration zone and separated into an organic phase containing dinitrotoluene and a second spent acid phase, the improvement which comprises:

effecting the formation of dinitrotoluene in at least two dinitration stages comprising at least one intermediate dinitration zone and at least one dinitrotoluene polishing zone;

removing the reaction product from said dinitrotoluene polishing zone and separating said reaction product into a crude dinitrotoluene product and a third spent acid phase;

utilizing a feed source of sulfuric acid for said process containing from about 86 to 91 percent by weight of sulfuric acid; and, introducing at least a portion of said feed source of sulfuric acid and said nitric acid to said dinitrotoluene polishing zone.

2. The process of claim 1 wherein the conversion of mononitrotoluene to dinitrotoluene in said intermediate dinitration zone is maintained at a level from 60 to 95 mole percent.

3. The process of claim 2 wherein the concentration of sulfuric acid in said first spent acid is maintained at a level of from about 70 to 74 percent by weight.

4. The process of claim 3 wherein at least a portion of said second spent acid is introduced to the mononitration zone for converting toluene to mononitrotoluene.

5. The process of claim 4 wherein al least a portion of said third spent acid is introduced to said intermediate dinitration zone for converting at least a portion of said mononitrotoluene to dinitrotoluene.

6. The process of claim 5 wherein the feed source of nitric acid for said process has a concentration of from 57 to 69 percent by weight.

7. The process of claim 6 wherein the molar conversion of mononitrotoluene to dinitrotoluene in said intermediate dinitration zone is maintained at a level from about 80 to 95%.

8. The process of claim 7 wherein the concentration of nitric plus nitrous acid in said mononitration zone ranges from about 0.2 to 1.5 percent by weight on an organic-free basis.

9. The process of claim 8 wherein the sulfuric acid concentration of the feed source for said process is from about 87 to 89 percent by weight.

10. In a process for producing dinitrotoluene by the mixed acid nitration of toluene wherein toluene is contacted with a mixture of nitric acid and sulfuric acid under nitration conditions to form mononitrotoluene in a mononitration zone, the reaction product separated into an organic phase containing mononitrotoluene and a first spent acid phase, and said organic phase containing mononitrotoluene introduced to a dinitration zone wherein it is contacted with a second mixture of nitric acid and sulfuric acid under nitration conditions to convert said mononitrotoluene therein to dinitrotoluene, the reaction product removed from the dinitration zone and separated into an organic phase containing dinitrotoluene and a second spent acid phase, and further where at least a portion of the second spent acid is used to form said mixture of nitric acid and sulfuric acid for effecting nitration of toluene in said mononitration zone, the improvement which comprises:

effecting the formation of dinitrotoluene in at least two dinitration stages comprising at least one intermediate dinitration zone and at least one dinitrotoluene polishing zone;

removing the reaction product from said dinitrotoluene polishing zone and separating said reaction product into a crude dinitrotoluene product and a third spent acid phase;

utilizing a feed source of sulfuric acid containing from about 86 to 91 percent by weight of sulfuric acid;

introducing at least a portion of said feed source of sulfuric acid and said nitric acid to said dinitrotoluene polishing zone; and, utilizing said second spent acid for effecting dinitration of mononitrotoluene in said intermediate dinitration zone.

11. The process of claim 10 wherein the process utilizes a feed source of sulfuric acid having a concentration from about 87 to 89 percent by weight.

12. The process of claim 11 wherein the process utilizes a feed source of nitric acid having a concentration from about 57 to 69 percent by weight.

13. The process of claim 11 wherein the process utilizes a feed source of nitric acid having a concentration from about 90 to 98 percent by weight.

* * * * *